United States Patent [19]

Eisen et al.

[11] Patent Number: 6,002,741

[45] Date of Patent: Dec. 14, 1999

[54] TECHNIQUE FOR OBTAINING SUB-PIXEL SPATIAL RESOLUTION AND CORRECTED ENERGY DETERMINATION FROM ROOM TEMPERATURE SOLID STATE GAMMA AND X-RAY DETECTORS WITH SEGMENTED READOUT

[75] Inventors: Yosef Eisen, Nes Ziona; Asher Shor, Jerusalem, both of Israel

[73] Assignee: The State of Israel, Atomic Energy Commission Soreq Nuclear Research Center, Yavne, Israel

[21] Appl. No.: 08/992,672

[22] Filed: Dec. 17, 1997

[30] Foreign Application Priority Data

Dec. 20, 1996 [IL] Israel ......................................... 119875

[51] Int. Cl.[6] .............................. G01N 23/04; G01T 1/24
[52] U.S. Cl. ................. 378/62; 250/370.01; 250/370.09; 250/370.1
[58] Field of Search .................. 378/19, 62; 250/370.01, 250/370.08, 370.09, 370.1

[56] References Cited

U.S. PATENT DOCUMENTS

| | | | |
|---|---|---|---|
| 5,365,069 | 11/1994 | Eisen et al. | 250/370.09 |
| 5,440,130 | 8/1995 | Cox et al. | 250/370.09 |
| 5,528,043 | 6/1996 | Spivey et al. | 250/370.09 |
| 5,693,947 | 12/1997 | Morton | 250/370.09 |
| 5,825,033 | 10/1998 | Barrett et al. | 250/370.1 |
| 5,887,049 | 3/1999 | Fossum | 378/98.8 |

FOREIGN PATENT DOCUMENTS 105881  1/1993  Israel .

OTHER PUBLICATIONS

"Current state-of-the-art industrial and research applications using room-temperature CdTe and CdZnTe solid state detectors", Y. Eisen; Nuclear Instruments and Methods in Physics Research; 380, (1996), pp. 431–439.

"Correction of incomplete charge collection in CdTe detectors"; Eisen et al., Nuclear Instruments & Methods in Physics Research, 353, (1994), pp. 60–66.

"Single–polarity charge sensing in ionization detectors using coplanar electrodes", P. N. Luke, Nov., 1994. Appl. Phys. Lett. 65.

"A new 2–dimensional high resolution Si detector for B–and γ–radiograpy", A. Czemak et al., Nuclear Instruments and Methods in Physics Research, 360, (1995), pp. 290–296.

"Some New Developments in the Field of High Atomic Number Materials", M. Cuzin, Nuclear Instruments and Methods in Physics Research 253 (1987) pp. 407–417.

"$Cd_{1-x}Zn_xTe$ Gamma Ray Detectors", J. Butler et al., IEEE Transactions on Nuclear Science, vol. 39, No. 4, 1992 pp. 605–609.

"Charge Transport in Arrays of Semiconductor Gamma–Ray Detectors", H. Barrett et al., The American Physical Society, vol. 75, No. 1, Jul. 3, 1995, pp. 156–159.

*Primary Examiner*—David Vernon Bruce
*Attorney, Agent, or Firm*—Oliff & Berridge, PLC

[57] ABSTRACT

A method and apparatus for obtaining the planar location with sub-pixel resolution and corrected energy of a gamma or X-ray photon interacting with a room temperature solid state detector of given thickness. The detector comprises two electrodes of negative and positive polarities. One of the electrodes is common, and the other is segmented being formed with segmented readout elements. Each of the readout elements defines a pixel size. Depending on that the negative or positive electrode is segmented, respectively, negative-induces charge signals are induced on the readout elements or both a positive-induced charge signal is induced on a central readout element and negative-induced charge signals are induced on adjacent readout elements. Accordingly, respective induced-charge signals are simultaneously measured and statistically correlated on the respective readout elements with detector response templates so as to obtain a best fit template, thereby determining the photon's energy, location and depth of interaction.

22 Claims, 9 Drawing Sheets

TECHNIQUE FOR OBTAINING SUB-PIXEL SPATIAL RESOLUTION AND CORRECTED ENERGY DETERMINATION FROM ROOM TEMPERATURE SOLID STATE GAMMA AND X-RAY DETECTORS WITH SEGMENTED READOUT

FIELD OF THE INVENTION

The present invention relates to gamma and X-ray spectroscopy and imaging using room temperature solid state detectors with segmented readout.

BACKGROUND OF THE INVENTION

Solid state gamma and X-ray detectors are used for many applications which require precise spectroscopic measurements. These applications include security, medical, space and astrophysical research, reactor safety, and host of others. A gamma or X-ray interacting with a solid state detector produces secondary ionizing radiation which create electron-hole pairs. The number of electron-hole pairs produced is directly proportional to the energy of the absorbed gamma or X-ray. Under the influence of the electric field existing between the electrodes of the detector the electrons and holes drift towards the positive and negative electrodes, respectively, where they are collected. The drifting electrons and holes induce signals on the electrodes which are amplified. The induced are proportional to the energy of the absorbed gamma or X-ray, and thus good spectroscopic measurements are obtained. Solid state detectors and their associated electronics tend to be compact, require little power, and their stabilization time is small.

For very accurate spectroscopic measurements, germanium detectors (i.e. Ge(Li) ) are used (see, for example, F. S. Goulding, Nuclear Instruments and Methods, Vol. 43, pp. 1–54, 1966). These detectors provide very accurate energy measurements because of the low energy required to produce an electron-hole pair, and the correspondingly large number of electron-hole pairs produced per gamma or X-ray interaction. Germanium detectors must be operated at liquid nitrogen temperatures because of the very small energy band gap. Since they operate at liquid nitrogen temperatures, mobilities are high and charge collection efficiencies are effectively unity for both electrons and holes. Imaging systems with germanium detectors exist, but are costly because the whole imaging system needs to be at liquid nitrogen temperature.

Gamma and X-ray detectors and imaging system have also been made from silicon. For gamma or X-rays with energy above 20 keV, silicon suffers from its low photoelectric absorption probability, due to its low atomic number, Z=14. Nonetheless, silicon detectors are very useful for gamma and X-rays with energies less than 20 keV. Recently, imaging system prototypes have been made from silicon with readout segmented onto strips or pads of 50–100 $\mu$m spacing (see, for example, A. Czermak, et al., Nuclear Instruments and Methods, Vol. A360, pp. 290–296, 1995.). Spatial resolutions of several $\mu$m have been achieved by determining the centroid of collected charge distribution on the strips or pads. The physical effect which distributes the collected charge (electrons or holes) among several strips or pads is the diffusion of the charges as they drift in the electric field towards the electrodes. The transverse diffusion of the charge carriers typically expands over an area of about 50–100 $\mu$m.

Much effort has gone to developing room temperature solid state detectors with medium to high atomic number. Some of the materials which have shown promise are: CdTe, CdZnTe, Hgl2GaAs, PbI2 (M. Cuzin Nuclear Instruments and Methods, Vol. A253, pp. 407–417, 1987; Y. Elisen, Workshop on Solid State Gamma and X-ray Detectors, Grenoble, September 1995, to be published in Nuclear Instruments and Methods). These materials have a high absorption probability, even for gamma rays with energies above 100 keV. Room temperature operation is a very important consideration in many applications. However, these materials suffer from bad to poor charge transport properties for the holes. As a result, detectors from these materials exhibit incomplete charge collection properties, whereby only a fraction of the photoelectric conversions appears in a distinct photopeak, and the rest of the events show up in a broad "incomplete" low energy region. To correct for this many techniques, both in hardware and software, have been developed. One of the more popular schemes, especially for CdTe detectors, involves correlating lower charge collection with longer risetimes of the pulses. The longer risetimes indicates a deeper interaction of the gamma or X-ray in the crystal which requires a larger fraction of the collected charge to be induced by the holes (see, for example, Y. Eisen and Y. Horowitz, Nuclear Instruments and Methods, Vol. A353, pp. 60–66, 1994).

A lot of emphasis has been placed on developing imaging systems utilizing room temperature solid state detectors. Imaging systems have been constructed with an array of individual detector elements, where each detector element forms a pixel of the imaging systems. Monolithic solid state detectors with segmented readout, usually with pad segmentation, with each pad serving as a pixel in the imaging system, have also been developed. Segmentation of the readout in monolithic detectors is convenient and economic in that it saves a lot of processing and machining of the detector material during production.

More recently, attention has been focused on CdZnTe as a promising material for room temperature solid state gamma and X-ray detectors (see, for example, J. F. Butler, C. L. Lingren, and F. P. Doty, IEEE Trans. Nuclear Science, Vol. 39, No. 4, pp. 605–609, 1992). CdZnTe has relatively high mean atomic number (Z-50 as compared Z=32 for germanium). It also has very high resistivity, $p \approx 10^{11}$ $\Omega$-cm, and as a result very low leakage current. Low leakage current means very little noise, and insensitivity to changes in temperature (i.e. dark current).

CdZnTe detectors, despite exhibiting excellent charge transport properties for electrons, show fair to poor charge transport properties for holes. As a result techniques for obtaining good spectroscopy using only the induced signals from the electrons have been developed, irrespective of the holes or depth of interaction. A scheme employing parallel grids at the anode, which is sensitive to the electron signal only has been developed (P. Luke, Applied Phys.Lett., Vol. 65, pp. 2884–2886, 1994). This scheme requires fine segmentation of the positive electrode into strips with a small difference in bias between alternating strips. The electrons are collected on the strips with the slightly higher bias.

An approach using small segmented readout elements at the anode has also been developed (H. H. Barrett, J. D. Eskin, and H. B. Barber, Phys.Rev,Lett., Vol. 75, pp. 156–159, 1995). In this approach, the smaller the readout element size the less the sensitivity to incomplete charge collection of the holes, since the small readout element would only feel induced charge from electrons drifting in close vicinity to the readout element. This approach obviously also benefits from the very fine spatial resolution accorded by the small readout elements, although at the cost of large number of channels of electronics and also the corresponding slowness in readout acquisition time.

Solid state detectors hold the potential of very fine spatial resolution, and therefore very good imaging capabilities. The compactness of solid state detectors and the readout electronics enable fabrication of small detector elements, where each detector element in an array of detectors can comprise a pixel of the image formed. Imaging systems have been constructed with individual solid state detector elements of sizes as small as 1 mm. A more economical solution, which avoids individual processing of each detector element at the manufacturing stage, is to fabricate monolithic solid state detectors with segmented readouts, where either the positive or negative electrode is segmented in any desired fashion dictated by the readout requirements. Each detector readout element has its own charge sensitive electronics. Readout electrodes in monolithic solid state detectors are typically segmented into pad (i.e., square) elements or strip elements, although other segmentation geometries can be applied. Usually, in a pad segmentation configuration, the position of the incident X-ray or gamma ray in the image is obtained from the planar location of the pad which received the signal within the array. In such a case, the spatial resolution of the image is limited to the size of the pad. Smaller pad elements can therefore lead to better spatial resolution, but with an quadratic increase in detector segmentation and a correspondingly quadratic increase in cost of readout electronics and readout complexity. Readout from segmented electrodes, especially in silicon detectors, has also been configured in strip geometry. Strip geometry enables a finer spatial resolution with only a linear increase in segmentation (and therefore price of electronics), but at the cost of requiring projective readout with the ambiguities and slow readout inherent in projective readout. Additional shortcomings of strip readout include inability to handle high counting rates, and growth of noise with increased detector area. Simultaneous x and y measurement can be accomplished by using double sided strip readout, with the strips on one side of the detector perpendicular to the strips on the other side.

It is an object of the present invention to provide a method for obtaining image spatial resolution smaller than the readout element size (i.e., sub-pixel resolution) of a segmented room temperature solid state detector, thereby affording improved image resolution without incurring the costs involved in using smaller readout elements.

It is a further object of the present invention to provide a method for correcting the incomplete charge collection and improving the energy resolution of a room temperature solid state detector, provided the detector has segmented readout. This will lead to much better spectroscopic performance of the detector. An imaging system comprising of superior spectroscopic detectors will provide for improved image contrast.

GLOSSARY

In the following description and claims the following terms will be used:

Photon—will be used to denote either a gamma or an X-ray photon.

Central readout element—the readout element whose area encompasses the point of interaction of the photon. In a detector in which the positive electrode is segmented, the central readout element detects the maximum positive induced charge signal. In a detector in which the negative electrode is segmented, it is the readout element that detects the maximum negative induced charge.

Adjacent readout element—in a detector with segmented readout elements, any readout element which is not a central readout element. For a detector which exhibits hole trapping the adjacent readout elements receive negative signals, irrespective of whether the segmented electrode is the positive or negative electrode.

Template—a pre-measured detector response map for a detector with segmented readout elements. A template can be obtained by measuring the simultaneous induced charge distribution on all segmented elements with a well controlled setup scanning the x-y position with a well collimated mono-energetic photon source, or by theoretical considerations.

Planar location—the location of an object in a plane. For the sake of clarity detectors will be oriented with respect to a rectangular cartesian coordinate system so that their electrodes are parallel to the X,Y plane of the coordinate system. The planar location of an object is given by the X,Y coordinates of the object in the coordinate system.

Positive signal—the positive-induced electric charge distribution on an electrode or segmented readout element due to drifting electrons.

Negative signal—the negative-induced electric charge distribution on an electrode or segmented readout element due to the holes.

Depth of interaction—in a detector, oriented with respect to a rectangular cartesian coordinate system so that its electrodes are parallel to the X,Y plane of the coordinate system and the electrode on which a photon is incident is taken as the plane Z=0, the Z coordinate of the point of interaction of the photon with the detector at which electron/hole pairs are formed.

Surface of revolution—a distribution of induced charge on the surface of an electrode, with azimuthal symmetry in x-y, in which concentric isocontours define equal potentials which increase towards the point where photon interaction occurred.

SUMMARY OF THE INVENTION

The invention makes use of room-temperature solid state gamma and X-ray detectors having two electrodes. The detector is held at either a positive or negative bias, that is one electrode (the positive electrode) is positive relative to the other (the negative electrode). This bias creates an electric field between the electrodes. Within the scope of this invention, one of the electrodes, either the positive or the negative one, comprises an array of readout elements, i.e. the electrode is segmented.

A photon incident on the detector will interact with the solid state material of the detector creating electron/hole pairs. The operating conditions of the detector are chosen such that the electrons are almost completely collected and the holes are almost completely trapped. Hence, under the influence of the electric field the electrons will drift towards the positive electrode and be collected whereas the holes will drift only slowly towards the negative electrode with a relatively high probability of becoming trapped along the way.

For the case where the positive electrode is segmented the drifting electrons give rise to a well localized positive-induced electric charge distribution (i.e., positive signal) on the segmented elements of the positive electrode, whereas the trapped holes give rise to a broad negative-induced electric charge distribution (i.e., negative signal). The two signals are superimposed so that in the region of overlap the positive signal is reduced in magnitude by the presence of the negative signal. The lateral width of the distribution of the positive signal is normally much smaller that the dimensions of a segmented element. (Since the electrons are essentially collected, the lateral width of the positive induced charge is due solely to the lateral scatter of the electrons as they drift towards the positive electrode. This spread is of the order of 50–100 microns). In contrast, the negative induced charge due to the trapped holes can cover several readout elements.

In a detector with segmented readout elements the location of the region of interaction of the incident gamma or X-ray is given by the planar location of the segmented element on which the maximum positive signal is induced. Since the readout electronics integrates the charge distributed on the readout element, the spatial resolution is limited to the dimension of the segmented element.

Furthermore, if the positive induced signal on the central readout element was due to the drifting electrons only then the magnitude of the positive induced signal on the central readout element would be proportional to the energy of the incident gamma or X-ray. However, the positive induced signal on the central readout element is a superposition of the positive induced signal due to the drifting electrons and the negative induced signal due to the trapped or slowly moving holes. Hence, the value of the energy of the incident gamma or X-ray as deduced from the positive induced signal on the central readout element will be less than actual photon energy (i.e. incomplete charge collection).

For the case where the negative electrode is segmented the drifting electrons gives rise to a positive-induced electric charge distribution on the non-segmented positive electrode only, whereas the trapped holes again give rise to a negative-induced charge distribution on the segmented elements of the negative electrode. Since the holes are not completely collected, the deduced value for the energy of the incident gamma or X-ray will be less than the actual energy of the photon.

There is, therefore, a necessity for improving the performance of existing room temperature solid state gamma and X-ray detectors, both with respect to the determination of the location of an interacting gamma or X-ray photon and with respect to the determination of its energy.

In accordance with the present invention there is provided a method for obtaining the planar location with sub-pixel resolution and corrected energy of a photon interacting with a room temperature solid state detector of given thickness having a positive electrode with segmented readout elements wherein a maximum positive-induced charge signal is induced on a central readout element and negative-induced charge signals are induced on adjacent readout elements, said method comprising the steps of:

for each photon interaction trigger, measure signals from all detector segments simultaneously, measuring the positive-induced charge signal on the central readout element and the negative-induced charge signals on the adjacent readout elements; and statistically correlating the positive-induced charge signal on the central readout element and the negative-induced charge signals on the adjacent readout elements with detector response templates to obtain a best fit template thereby obtaining the photon's energy, location and depth of interaction.

Typically, for detectors having a positive electrode with segmented readout elements, said templates are constructed by measurement in accordance with the following steps:

irradiate the room temperature solid state detector with a photon of known energy and a given planar location;

collect a sample of photon interaction events, where for each photon event measure simultaneously the maximum positive-induced charge signal induced on the central readout element and the negative-induced charge signals induced on the adjacent readout elements;

store the known energy and planar location of the incident photon and the sample of photon interaction events containing the maximum positive-induced charge and the negative-induced charge signals in memory means;

compute for each of the sample of photon interaction events the measured energy of the incident photon by summing the positive and negative-induced charge signals on the readout elements;

derive for each of the sample of photon interaction events the depth of interaction from the thickness of the detector, the measured and the known energy of the incident photon; and after completing these steps for creating a template at this specific x-y location, scan the detector at various x-y locations and repeat the above steps at each x-y location to obtain a detector map of templates of detector response.

Also in accordance with the present invention there is provided a method for obtaining the planar location with sub-pixel resolution and corrected energy of a photon interacting with a room temperature solid state detector of a given thickness having a common positive electrode and a negative-induced charge signal is induced on said readout elements, said method comprising the steps of:

simultaneously measuring the negative-induced charge signal on said readout elements;

statistically correlating the negative-induced charge signal on the readout elements with templates to obtain a best fit template thereby obtaining the photon's location and depth of interaction;

obtaining the total negative-induced charge on the readout elements; and hence a measured energy of the incident photon; and deriving a corrected energy of the incident photon from the measured energy, depth of interaction and thickness of the detector.

Typically, for detectors having a negative electrode with segmented readout elements, said templates are constructed by measurement in accordance with the following steps:

irradiate the room temperature solid state detector with a photon of known energy and planar location;

collect a sample of photon events, where for each photon event measure simultaneously the negative-induced charge signals induced on the readout elements;

store the known energy and planar location of the incident photon and the sample of events containing the negative-induced charge signals in memory means;

derive for each of the sample of events the depth of interaction from the negative-induced charge signals where the depth of interaction, t, is equal to $D(1-E_{measured}/E_{photon})$ and D=thickness of detector, i.e. distance between the positive and negative electrodes, and store the result in the memory means; and after completing these steps for creating a template at this specific x-y location, scan the detector at various x-y locations and repeat the above steps at each x-y location to obtain a detector map of templates of detector response.

If desired, the statistical correlation is a $\chi^2$ correlation.

Further in accordance with the present invention there is provided a method for obtaining the planar location with sub-pixel resolution and corrected energy of a photon interacting with a room temperature solid state detector of given thickness having a positive electrode with segmented readout elements wherein a maximum positive-induced charge signal is induced on a central readout element and negative-induced charge signals are induced on adjacent readout elements, said positive and negative-induced charge signals being measured relative to a zero charge level, said method comprising the steps of:

interpolating the negative-induced charge signals induced on adjacent readout elements to obtain a surface of revolution of the interpolated negative-induced charge signals, said surface of revolution having a centroid and an apex;

determining the planar location of said centroid thereby obtaining the planar location of the photon interaction;

extrapolating the negative-induced charge contribution to the signal from the central readout element from interpolating the surface of revolution formed by adjacent readout elements to interpolated value on central readout element; and obtaining a corrected energy value by adding the magnitude of the extrapolated negative contribution to he signal obtained from the measured positive signal on the central readout element.

Still further in accordance with the present invention there is provided a method for obtaining the planar location with sub-pixel resolution and corrected energy of a photon interacting with a room temperature solid state detector of given thickness having a negative electrode with segmented readout elements wherein negative-induced charge signals are induced on the readout elements, said method comprising the steps of:

interpolating the negative-induced charge signals induced on the central and adjacent readout elements to obtain a surface of resolution of the interpolated negative-induced charge signals, said surface of revolution having a centroid;

determining the planar location of said centroid thereby obtaining the planar location of the photon interaction;

computing the measured energy of the incident photon by summing the negative-induced charge signals on all the readout elements determining the width of the body of revolution at its centroid, thereby obtaining the depth of the interaction; and obtaining a corrected energy value from the measured energy, the depth of interaction and thickness of the detector.

If desired, said simultaneous measurement is performed by triggering the detector when a trigger signal is obtained from the common (non-segmented) electrode.

Typically, said trigger signal is initiated at 15% of the energy of the signal detected on the common electrode.

Alternatively, said simultaneous measurement is performed by triggering the detector when a trigger signal is obtained from any one of the segmented readout elements by means of a discriminator placed in each readout channel.

If desired, said trigger signal is initiated at a predetermined level of the energy of the signal detected by said any one of the segmented readout elements.

Typically, said trigger signal is initiated at 15% of the energy of the signal detected by said any one of the segmented readout elements. When a trigger signal is obtained, all the readout elements are strobed simultaneously.

BRIEF DESCRIPTION OF THE DRAWINGS

For a better understanding the invention will now be described by way of example only with reference to the accompanying drawings, in which:

FIG. 1a shows the induced surface charge distribution on the positive electrode and FIG. 1b shows the induced surface charge distribution on the negative electrode;

DETAILED DESCRIPTION OF THE INVENTION

The description of the invention will be preceded by a brief description of the physical processes occurring as a result of a gamma or X-ray interaction with a room temperature solid state detector.

Assume, without limiting the generality, a gamma or X-ray incident on a solid state detector is totally absorbed via the photoelectric effect. It produces secondary ionizing radiation which generate $N_0$ electron-hole pairs within very close proximity (on order of 50–100 microns). The number of pairs produced, $N_0$, is directly proportional to the energy of the incident gamma or X-ray. For a solid state detector with complete charge collection, measuring the total electron and hole induced charge thereby provides spectroscopic information on the incident gamma or X-ray. The induced signal is very well localized (to within 50–100 microns), so very fine segmentation of the readout is necessary, if accurate spatial information of the incident gamma or X-ray is required.

Unfortunately, all room temperature solid state detectors with medium to high atomic number suffer from incomplete charge collection. As a result of charge trapping, not all the charge carriers make it to the collecting electrodes, and as a result, the induced charge is less than $qN_0$. For most of the room temperature detectors, a high rate of hole trapping is exhibited, and thereby the induced charge for a monoenergetic gamma or X-ray source will depend on the depth of interaction in the detector. In the limit of total electron collection and complete hole trapping, the decrease in induced charge will linearly depend on the depth of the gamma or X-ray interaction (for gamma/X-rays incident on the negative electrode). For example, integration at midpoint between negative and positive electrode will result in only half of the maximum possible induced charge.

The present invention exploits the phenomena of incomplete charge collection on condition that the detector still exhibits good electron transport properties. For detectors with segmented readout hole trapping cause induced signals to appear also on adjacent readout elements. Analysis of the charge sharing profiles on adjacent readout elements can provide sufficient information for correcting the measured energy and for determining the location of the gamma or X-ray interaction to high precision, often to within a small fraction of the dimensions of the readout elements. The effect behind the invention is maximized for detectors which have high electron collection and poor hole collection (i.e. large hole trapping and/or hole transit times much larger than the time scale of the integrating electronics. Detectors such as CdZnTe can easily be operated in regimes of applied voltages and electronic readout times in which this condition is more or less realized. It should be noted that the present invention can also be applied to detectors which exhibit less pronounced hole trapping, but the desired effect is correspondingly less pronounced.

The conditions of complete, or almost complete, electron collection simultaneous with complete, or almost complete, hole trapping is easily achievable for most room temperature solid state detectors. For example, CdZnTe detectors of, say, 3 mm in thickness can be operated at 50 V, yielding an electronic field across the detector ($E_d$) of 167 V/cm. The electron mobility times trapping time ($\mu_e\tau_e$) will be between $3\times10^{-3}$ and $10^{-2}$ cm$^2$/V and the hole mobility times trapping time ($\mu_h\tau_h$) will be less than $10^{-4}$ cm$^2$/V. The electron mean free path ($\lambda=E_d\mu_e\tau_e$) is therefore in the range of 5 to 16.7 mm, while the hole mean free path is less than 0.167 mm. Already, under these conditions, it is apparent that most of the electrons are collected and the holes are essentially trapped. Furthermore, with electronic shaping times of approximately 2 µs, whatever signal is induced by the holes is filtered out, since the hole transit time. ($D/E_d\mu_h$) is of the order of 36 µs, while for electrons the transit time is of the order of 1.8 µs. It should be stressed that operating conditions where almost complete electron collection and almost complete hole trapping exists is not essential for obtaining improved spatial and energy resolutions, but is preferred for best results.

It will be assumed in the following, unless stated to the contrary, that it is the positive electrode of the detector that is segmented and that the gamma or X-rays are incident on the negative electrode. The gamma or X-rays are absorbed at a depth t inside the detector, which is exponentially distributed with the mean interaction depth depending on detector atomic number and on the energy of the incident gamma or X-ray. Secondary ionization produced by the absorbed gamma or X-rays creates $N_0$ electron-hole pairs, mostly within a vicinity of 50–100 microns. The electric field across the detector separates the electrons and the holes. As these charge carriers drift towards their respective electrodes, a surface charge is induced on the electrodes to maintain constant potential.

The induced charge distribution is a dynamic process, but the final induced charge distribution on the electrodes can be determined from the final position of the charge carriers, i.e. the electron and holes which were separated from each other by the electric field across the detector. The total induced surface charge on the positive electrode, i.e. the discontinuity across the surface, is equal, but opposite, to the total charge of the electrons. (The signals registered by the readout electronics is equal in sign to the induced charge which is brought to the electrode surface, for readout using charge sensitive inverting preamp. Therefore, the signals on the readout electronics due to drifting electrons, is a positive signal). The spatial distribution of the surface charge is just the lateral spread of the drifting electron, which amounts to 50–100 microns. Likewise those hole carriers which drift towards the negative electrode, register a negative signal on the readout electronics.

Consider now a solid state detector which exhibits large hole trapping. Assume for simplicity that all the electrons are collected on the positive electrode, while all the holes are trapped at the location of the initial point of the gamma or X-ray interaction. The electrons drift towards the positive electrode and induce a well localized induced charge distribution equal to $qN_0$. The holes, remain stationary within the time scale of the integrating electronics. The surface charge that the holes induce on the positive electrode is $-qN_0/D$, where D=thickness of detector and t=depth of gamma interaction in detector. This distribution is broad, on the order of $2(D-t)$, and can be calculated by electrostatic theory. Thus, a sharp positive charge distribution is induced on the positive electrode due to the drifting electrons, superimposed on a spatially broad negative distribution due to the trapped holes. The total induced charge on the positive electrode is as follows:

$$\frac{qN_0 - qN_0 t}{D} = \frac{qN_0(D-t)}{D}$$

On the negative electrode, the total induced charge is due to the holes only and is as follows:

$$\frac{-qN0(D-t)}{D}$$

with a broad distribution on the order of 2 t.

Figure 1A:
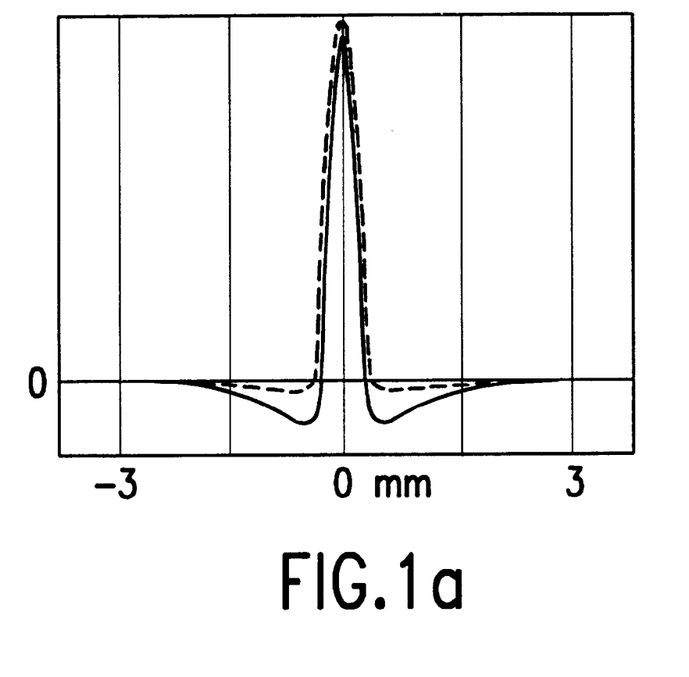
FIGS. 1a and 1b show examples of the calculated induced surface charge profiles on a single readout electrode for two interaction depths where
Figure 1B:
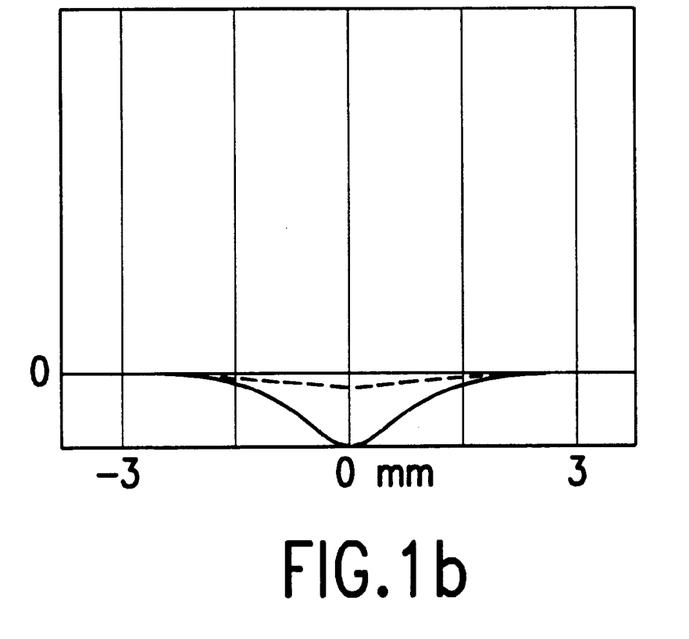

FIGS. 1a and 1b show examples of the calculated induced charge profiles on a single readout electrode for two interaction depths. The dashed line is for an interaction depth of 1 mm, whereas the continuous line is for an interaction depth of 2 mm. The detector thickness is taken as 3 mm. The gamma or X-ray photons are incident on the negative electrode at the x-y center of the electrode. Complete electron collection and complete hole trapping is assumed. The lateral spread of the electrons is taken to be 100 μm.

FIG. 1a shows charge sharing profiles as function of lateral distance from point of interaction on the positive electrode, for two photon interaction depths. Note a very sharp strong positive signal at the planar location of the gamma interaction, and a much broader but weaker negative distribution. The broad negative distribution is due to the trapped holes, whose contribution is largest for interactions closer to the positive electrode. It should be kept in mind that the actual induced charge distributions are circles of revolution around the point of interaction, i.e. the center of the distribution. For actual implementations involving segmented readout elements, the positive signal affects mostly one readout element, namely the central element, for element dimensions much larger than the transverse spread of the charge carriers. The much broader negative distributions affect several elements, and this forms the basis of the invention for obtaining sub-element spatial location of the interacting photons, as will be described in the following. Furthermore, the error in determining the energies of the incident photons, due to incomplete charge collection, can be corrected for from knowledge of the depth of the interaction which can be determined by comparing the magnitude of the positive signal with the negative distribution.

FIG. 1b shows the induced charge distribution on the negative electrode of the detector for two photon interaction depths. Note that there is only a negative component to this distribution, since the electrons are totally collected by the positive electrode. Interactions at depths closer to the negative electrode induce a stronger but narrower distribution. Actual implantations of segmented readout on the negative electrode can also provide good spatial resolution, although the energy correction will be inferior.

Examples of charge sharing profiles for detectors with segmented readout will now be given and it will be explained how these profiles can provide information on correct energy evaluation and sub-element spatial determination. For concreteness, a specific detector geometry and readout element geometry will be described, although it will be apparent that the invention has general application for all detectors with segmented readout.

Figure 2A:
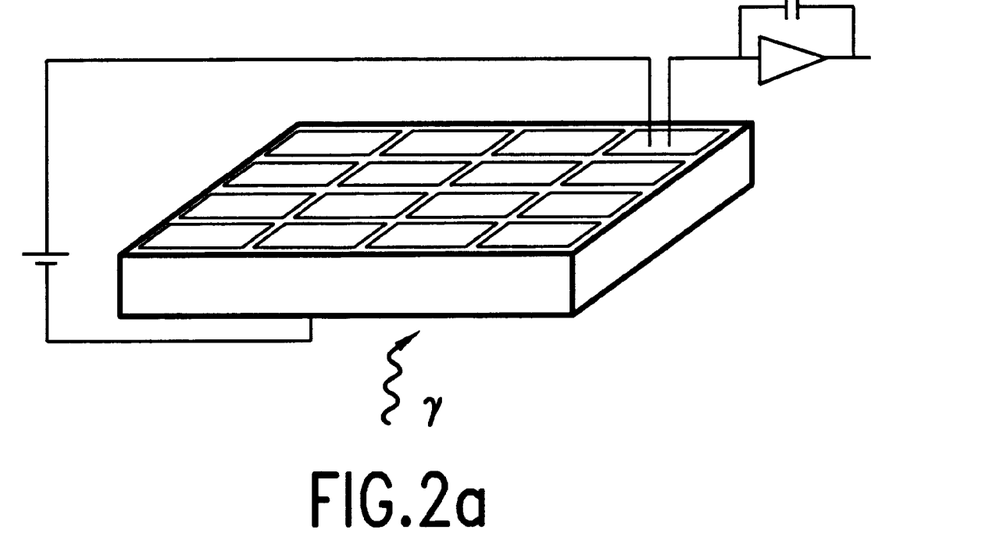
FIGS. 2a and 2b show the detector chosen to exemplify the charge sharing profiles, for this specific example, the detector is segmented on the positive electrode in a 4×4 pad array and each readout pad is connected to a charge sensitive amplifier.
Figure 2B:
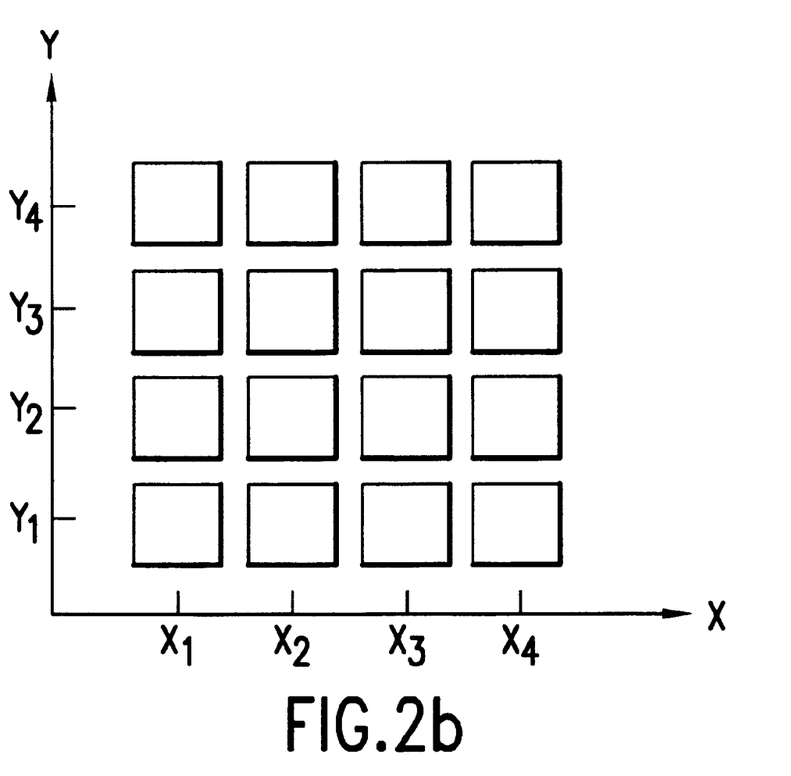

Attention is now drawn to FIGS. 2a and 2b showing the detector chosen to exemplify the charge sharing profiles. FIG. 2a shows a monolithic CdZnTe detector, 8×8 mm² in cross section and 3 mm thick, with a segmented positive electrode containing a 4×4 array of readout elements, where each readout element is 1.9×1.9 mm², with 0.1 mm spacing between elements. Each readout element is connected to its own low noise charge sensitive electronics. For the sake of illustration and in order not to clutter the figure, only one readout element is shown to be connected to low noise charge sensitive electronics, however it should be understood that each readout element is thus connected. Negative high voltage bias is placed at the common electrode. The gamma or X-ray photons are incident on the negative electrode (i.e. common). Each readout element is identified by the coordinates $X_i, Y_j$ (i=1, ..., 4; j=1, ... 4) of the center of the readout elements as shown in FIG. 2b, which shows a rectangular cartesian coordinate system superimposed on the segmented readout elements of the detector.

Each readout element defines a separate channel having charge sensitive electronics, typically a preamplifier, a shaper and an amplifier connected to it. (This scheme, depicting a transimpedance preamplifier, is not necessarily the only configuration. For example, one can have charge integrating electronics, although this is in general more noisy). When a gamma or X-ray interaction is registered, all channels are read out simultaneously. This can be achieved by triggering on the signal coming from the common electrode (the negative electrode if the positive electrode is the segmented electrode and vice versa). The signal from the common electrode triggers the readout if it is above a pre-determined threshold, say 15% of the full energy signal. If a trigger is registered, all readout channels are strobed when the peak of the common signal is detected. Alternatively, a discriminator can be placed on each channel of the segmented readout, and an event trigger is registered when any one of the readout channels is above the pre-determined threshold. All channels are strobed simultaneously at peak of trigger pulse. The analog information from each readout is digitized and the digital information from all readout channels is stored or transferred to a processor for further analysis.

Note that if the positive electrode is the segmented electrode, signals of both polarities will be read out. A positive signal will be detected on the "central" readout element, i.e. positive induced charge will be collected on the electrode surface, since the electrons drift towards this electrode. All other electrodes will register negative signals, i.e. negative induced charge accumulates on the readout electrode, since only the immobile holes generate induced charge on these readout elements. Occasionally, for gamma or x-ray interactions that occur between two readout electrodes, two (or more) readout elements will register positive signals corresponding to the drifting electrons, and all the rest will register negative signals corresponding to the trapped holes. In this case, the central readout element is taken as the combination of both readout elements containing a positive signal.

The readout electronics and digitizing scheme must be able to cope with both polarities. A simple method of achieving this is to have a constant positive voltage offset, so that the zero pedestal (i.e. no signal) will be at a positive channel after digitization. This positive offset must be larger in magnitude than all anticipated negative signals possible from adjacent readout elements. Given an analog to digital converter (ADC) for positive signals, so that positive signals will give positive ADC channels, any negative signal from adjacent readout elements will result in a non-zero ADC channel, but below the value of the pedestal channel.

Figure 3A:
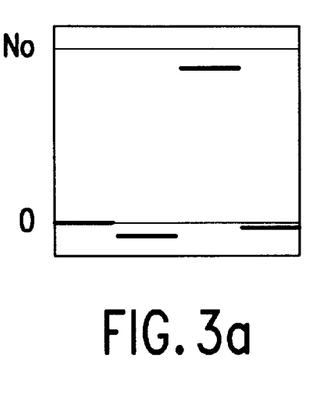
FIGS. 3a to 3c show the calculated induced surface charge for a row of readout elements of the detector shown in FIG. 2a for an interaction depth of 1.0 mm, FIG. 3a—photon at x=0.5 mm, FIG. 3b—photon at x=1.0 mm, FIG. 3c—photon at x=1.5 mm (relative to center of detector)
Figure 3B:
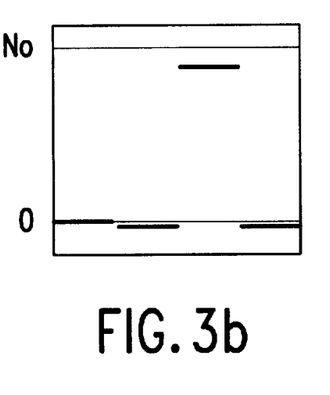
Figure 3C:
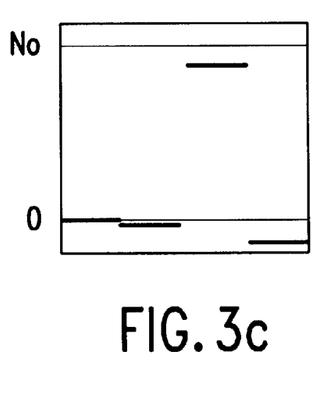
Figure 3D:
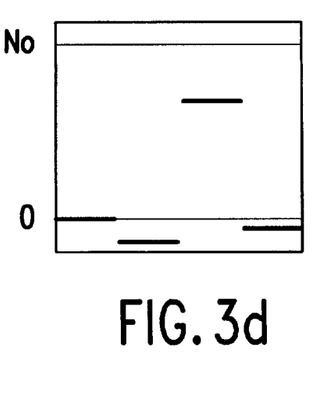
FIGS. 3d to 3f show the calculated induced surface charge for a row of readout elements of the detector shown in FIG. 2a for an interaction depth of 2.0 mm, FIG. 3d—photon at x=0.5 mm, FIG. 3e—photon at x=1.0 mm, FIG. 3f—photon at x=1.5 mm (relative to center of detector)
Figure 3E:
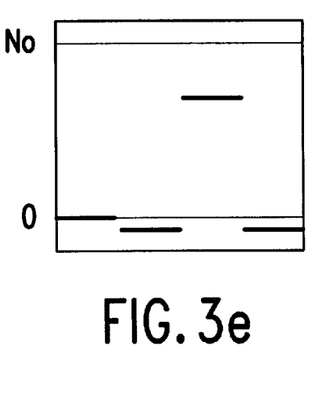
Figure 3F:
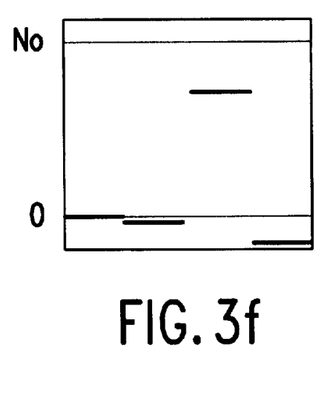

FIGS. 3a to 3c show the calculated responses (i.e., induced charge for given incident photon) of the readout elements $X_i$, $Y_j$, i=1, . . . , 4; j=3, for a photon incident at three points X,Y=(0.5, 1.0), (1.0, 1.0) and (1.5,1.0), respectively, and for an interaction depth of 1.0 mm. FIGS. 3d to 3f show the calculated responses for the same readout elements and for the same points of incidence of the photon, but for an interaction depth of 2.0 mm. The vertical scale in FIGS. 3a to 3f is in units of $qN_0$. The energy of the incident photon is 140 keV (yielding $N_0$~30,000). The cross hatch (between the two close parallel lines of some of the responses and almost not visible), shows the range of noise for $\sigma_{noise}$=150 $e^-$. Where $e^-$ is the charge on the electron.

It is noted that the spatial resolution of the segmented pad detector is equal to the dimensions of a readout element (if no correction is made). It is also noted that the maximum response induced on readout element ($X_3$, $Y_3$) is less than the incident photon energy (maximum is shown as dotted line in FIGS. 3a–3f). It is further noted that the magnitude of the negative signal on the adjacent readout elements varies as the planar location of the incident photon varies and also as the depth of interaction varies.

There exists, therefore, a correlation between the negative signals on adjacent read out elements and the positive signal on the center readout element. The present invention exploits this fact in order to increase the spatial resolution of detectors with segmented readout elements to within a fraction of the dimension of a readout element. No assumption has been made as to the shape of the readout elements. However, for imaging purposes, a square readout element is preferable in which case the dimension of the readout element is the length of the side of the readout element. The invention further exploits knowledge of the depth of interaction to correct the unmeasured photon energy, which is in error the incomplete charge collection. The depth of interaction is determined by correlating the magnitude of the positive signal on central pad, with the negative signals on adjacent pads. The increasing of the spatial resolution of the detector and the correction of the measured energy of the photon, will be collectively referred to as the improvement of the detector performance.

Detector performance can be improved by fairly straight forward interpolation methods, or by more complex statistical correlation methods.

Figure 4:
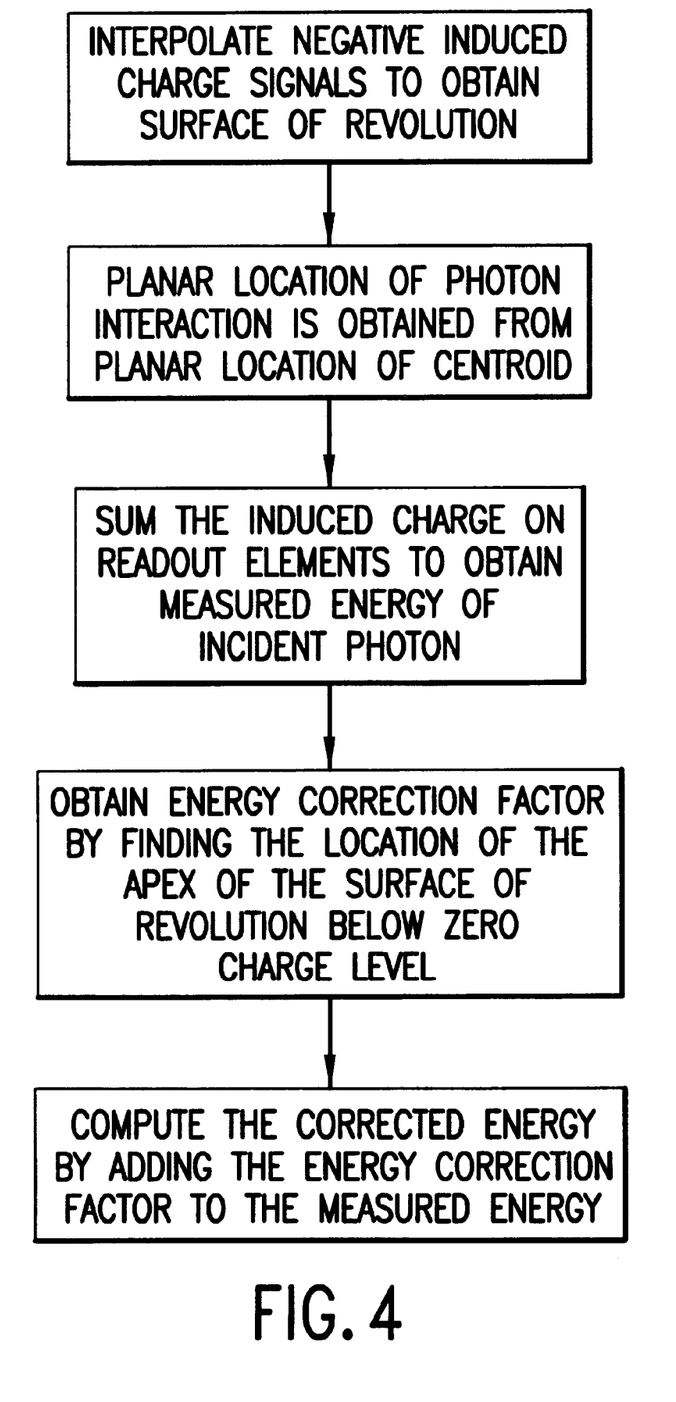
FIG. 4 shows a flow diagram of the main steps involved for improving detector performance of a detector with a segmented positive electrode using the interpolation method.
Figure 5:
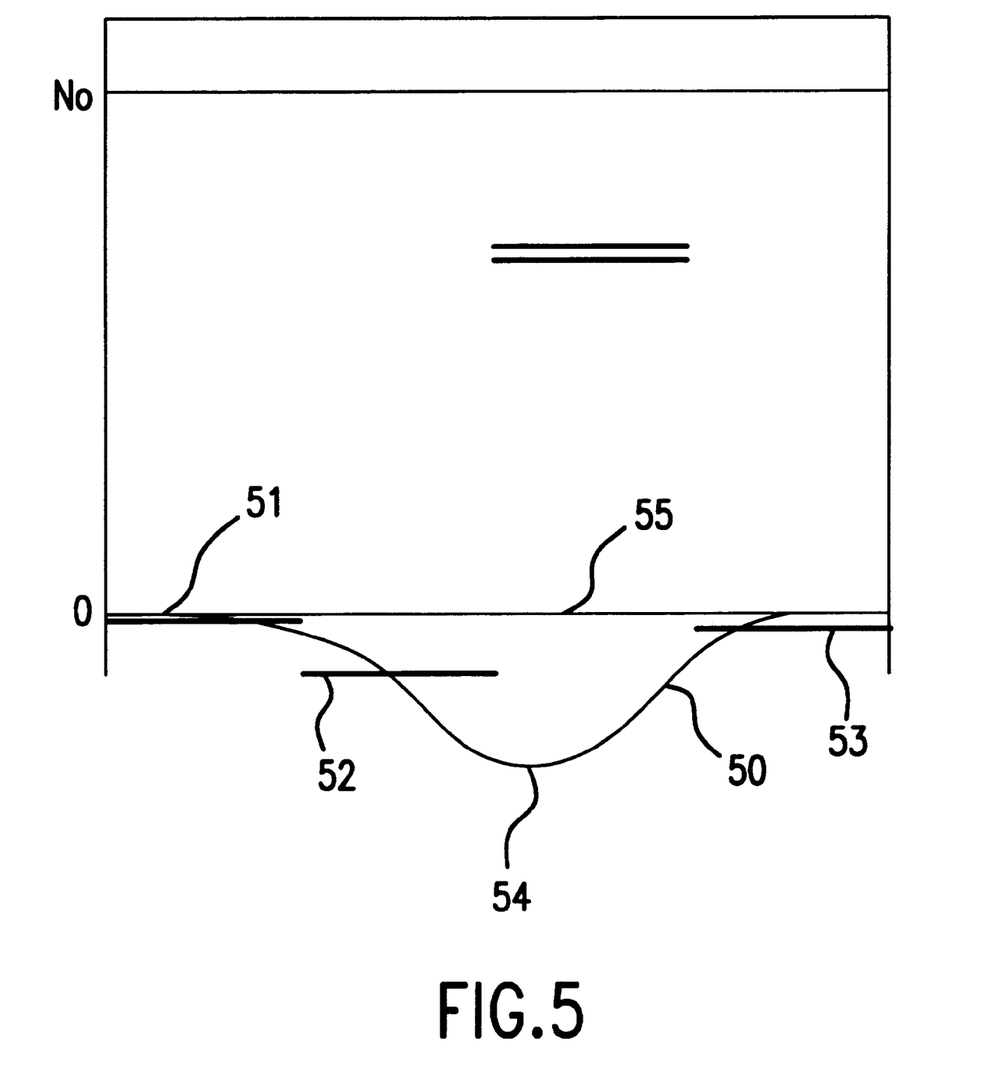
FIG. 5 shows a cross section of a surface of revolution obtained by interpolating the negative-induced charge signals induced on adjacent readout elements of a typical 4×4 segmented detector.

Attention is now drawn to FIG. 4, showing a flow diagram of the main steps involved for improving detector performance for a detector with a segmented positive electrode, using the interpolation method and, to FIG. 5, showing a cross section of a surface of revolution, obtained by interpolating the negative-induced charge signals 51, 52 and 53, induced on adjacent readout elements of a typical 4×4 segmented detector.

The Y-axis in FIG. 5 is the measured induced charge on the readout elements. The X-axis gives the location of the 4 readout elements of the 4×4 segmented detector in the plane, in which the cross section is taken.

The interpolation method involves interpolating the negative-induced charge signals induced on adjacent readout elements to obtain a surface of revolution of the interpolation negative-induced charge signals. The planar location of the centroid (apex) of the surface of revolution, is equal in value to the planar location of the photon interaction. The measured energy of the incident photon is computed by summing the positive and negative-induced charge signals on the readout elements. The energy correction factor can be obtained from the location of the centroid 54 of the surface of revolution below the zero charge level 55 of the induced charge, by taking into account the total integrated negative surface charge on the central readout element. The corrected energy value $E_{corrected}$ is obtained by adding the energy correction factor to the measured energy $E_{measured}$ on the central pad. Alternatively, the energy correction can be obtained by taking the ratio of the positive signal on the central readout element, and the sum of the negative signals on all adjacent readout elements. The ratio thus obtained is then compared to equivalent ratios stored in look up tables, which are generated by theoretical calculations, and from the comparison, the interaction depth, t, is obtained. In this case the corrected energy is derived from the following equation:

$$E_{corrected} = E_{measured} \cdot \frac{D}{D - t}$$

For a detector with a segmented negative electrode, the interpolation involves determining the centroid of the surface of revolution, formed from interpolating the negative-induced charge distribution on all readout elements. The planar location of the centroid, is the planar location of the photon interaction. The error in the measured energy of the photon due to incomplete charge collection, is determined by measuring the width at the centroid of the interpolated induced negative charge distribution on the readout elements. The width is of the order of 2t where t is the depth of the photon interaction. Hence, from the measured width, the depth t of the photon interaction can be extracted. The measured energy of the interacting photon is given by the total measured negative-induced charge on all the readout elements and the corrected energy is given by $E_{corrected}$= $E_{measured}$(D/(D−t), where D is the thickness of the detector.

The more precise statistical correlation method involves obtaining a statistical best-fit between the measured induced charge distribution on the readout elements and a set of templates.

Typically, a best least $\chi^2$ or maximum likelihood fit is used. The templates can be obtained either from theoretical considerations, or by carrying out well controlled experiments in which the planar location and energy of the incident photon are known, and the resulting induced charge distributions on the readout elements (also referred to herein as a detector response), are measured. Theoretical calculations of the induced charge on the central and adjacent readout elements can be obtained by calculating the induced surface charge on the electrodes induced by the drifting electrons and trapped hole carriers. An intuitive, but precise technique for this type of calculation, involves the method of images, a technique that is discussed in almost any book on electromagnetism.

Figure 6:
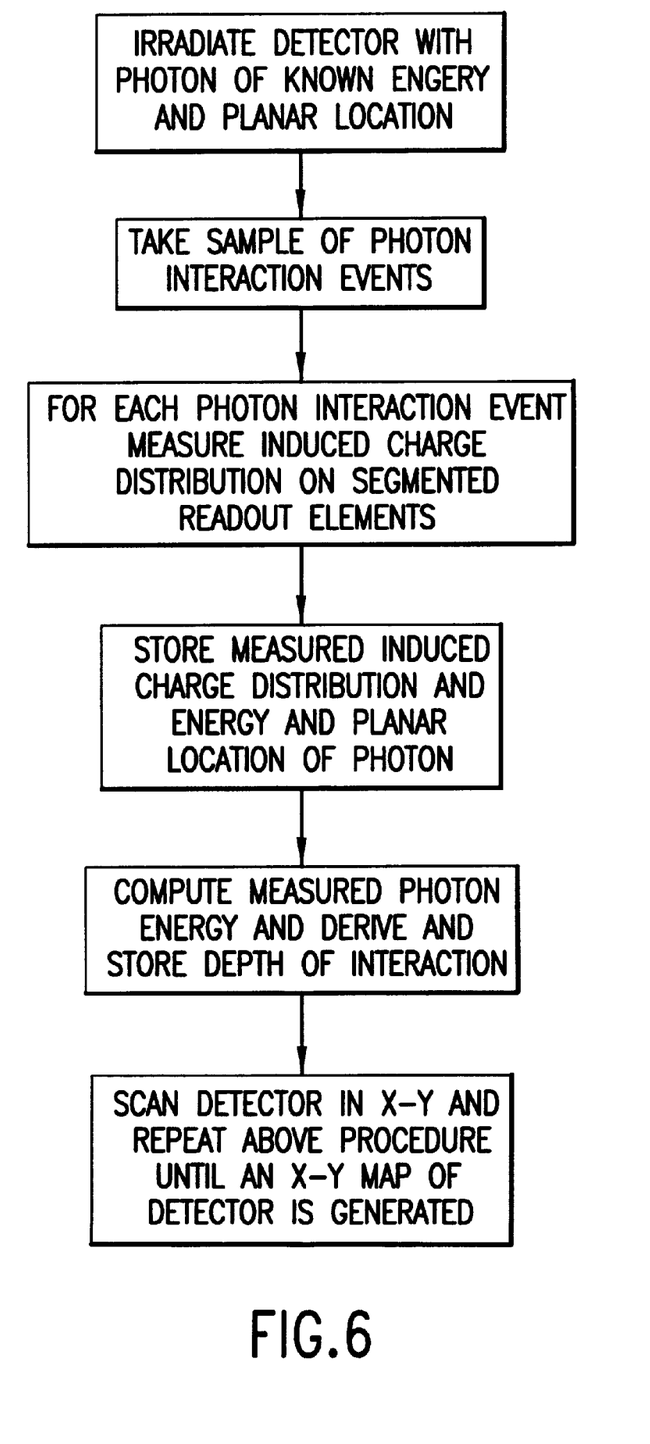
FIG. 6 is a flow chart of the main steps involved in constructing the templates.

The templates contain not only the planar location and known energy of the interacting photon but also the depth of interaction (Z=t), of the photon. The steps involved in constructing the templates are illustrated by the flow chart shown in FIG. 6. A detector for which templates are to be constructed, is irradiated with photon of known energy and known planar location. The detector is scanned with a well collimated gamma or X-ray photon source at various planar locations, so as to provide an x-y map of the detector response. At each planar location, a sample of photon interaction events are taken, since the depth of the photon's interaction is distributed over the detector's thickness. For each photon interaction, the resulting induced charge distributions on the segmented readout elements (i.e., the maximum positive-induced charge signal induced on the central readout element and the negative-induced charge signals induced on the adjacent readout elements) of the detector, are measured and then stored together with the known energy and planar location of the incident photon. The measured energy of the incident photon, which is proportional to the total induced charge distribution, is now computed by summing the measured charge distribution on the segmented readout elements. Finally, the depth of interaction, t, can be derived from the following equation:

$$E_{photon} = E_{measured} \cdot \frac{D}{D-t}$$

where $E_{photon}$ is the known energy of the incident photon in the controlled experiment, $E_{measured}$ is the measured photon energy and D is the thickness of the detector. The depth of interaction is then stored along with the induced charge distribution on the segmented readout elements and the known energy and planar location of the incident photon to complete the template.

Figure 7:
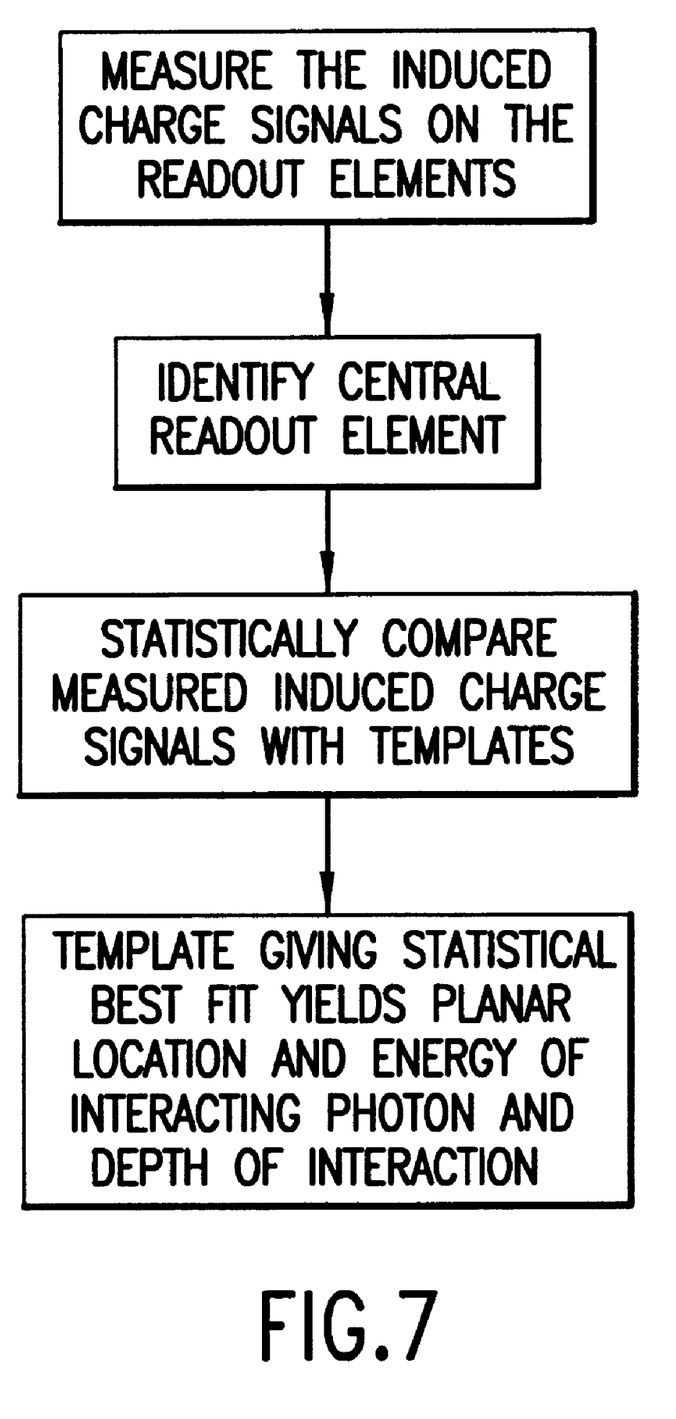
FIG. 7 shows a flow diagram of the main steps involved in obtaining improved detector performance for a detector with segmented positive electrode using the statistical method.

For a detector with segmented positive electrode, the main steps involved in obtaining improved detector performance, are illustrated in FIG. 7. Following the interaction of the photon with the detector, the induced charge signals on all the readout elements, are measured simultaneously. The central readout element is then identified as readout element with the maximum positive induced charge. In the next step, the measured induced charge signals are compared with templates of the detector response, and the template which best fits the measured signals to within one global normalization factor, is determined using statistical methods. The normalization factor is related to the energy of the interacting photon (i.e. the ratio of the interacting photon to that in the calibration measurement which produced the template). The planar location and energy of interacting photon and the depth of interaction, are given by the template giving the statistical best fit.

Figure 8:
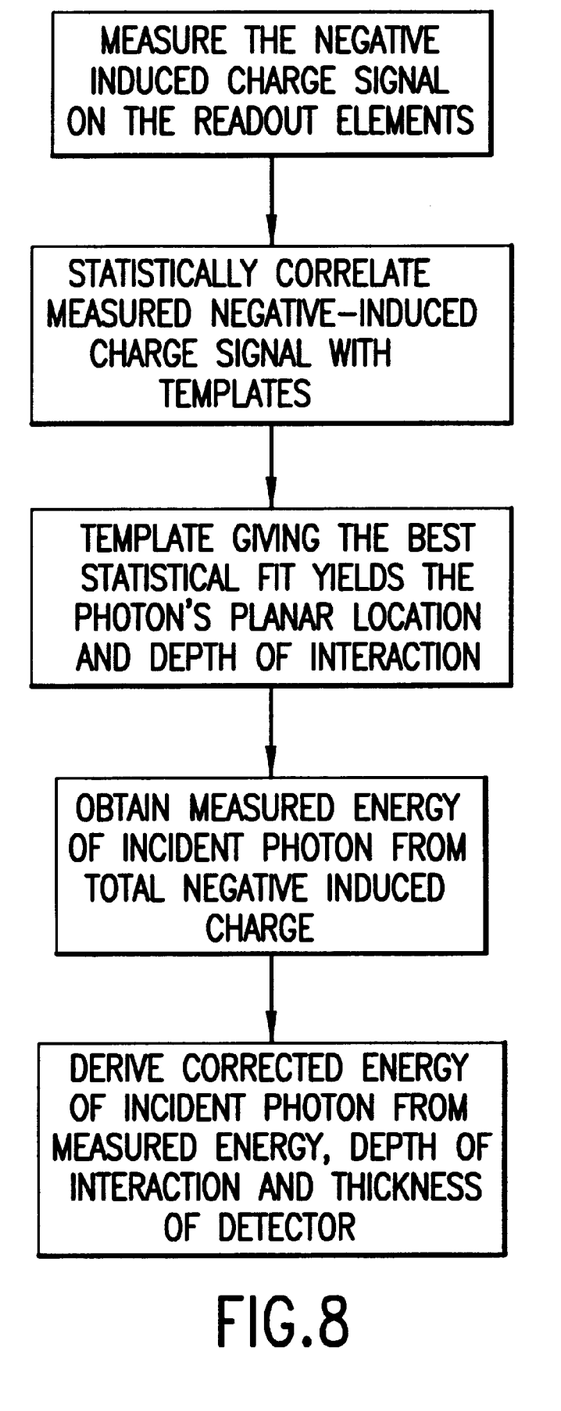
FIG. 8 shows a flow diagram of the main steps involved in obtaining improved detector performance for a detector with segmented negative electrode using the statistical method.

For a detector with segmented negative electrode, the main steps involved in obtaining improved detector performance are illustrated in FIG. 8. Following the interaction of the photon with the detector, the negative-induced charge signals on all the readout elements, are measured simultaneously. Next the measured induced charge signals are compared with templates of the detector response using statistical methods. The planar location and depth of interaction of the interacting photon are given by the template giving the statistical best fit. The measured energy, $E_{measured}$ of the incident photon, is derived from the total negative induced charge on the readout elements. The corrected energy of the photon is then obtained from the equation $E_{corrected}=E_{measured}(D/(D-t))$, where t is the depth of interaction and D is the thickness of the detector. For segmentation on negative electrode, the only parameter enabling correcting for the actual photon energy is the depth of the interaction, which is obtained from the lateral width of the induced charge distribution. In contrast, for segmentation, on positive electrode, the relative magnitude of positive induced charge on central pad, as compared to negative induced charge on adjacent pads, serves as a much more powerful means for correcting measured photon's energy.

Figure 9A:
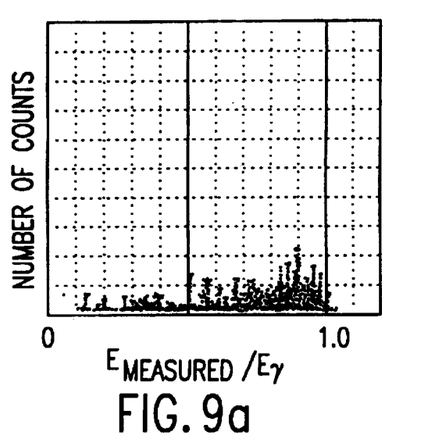
FIG. 9a shows the measured energy of gamma interaction for the monolithic detector array shown in FIG. 2a with uniform illumination of gamma rays with $E_\gamma$=140 keV with the detector operating in the mode of efficient electron collection and maximum hole trapping.
Figure 9B:
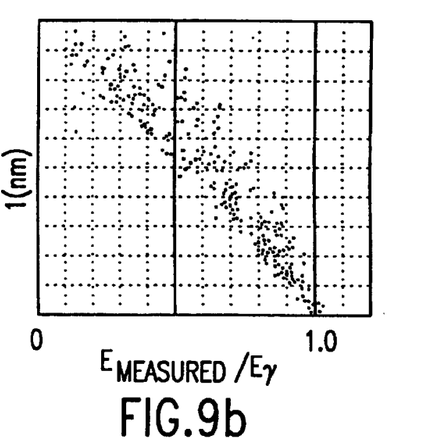
FIG. 9b shows the measured energy of gamma interaction correlated with the depth of interaction for the monolithic detector array shown in FIG. 2a with uniform illumination of gamma rays with $E_\gamma$=140 keV with the detector operating in the mode of efficient electron collection and maximum hole trapping.
Figure 9C:
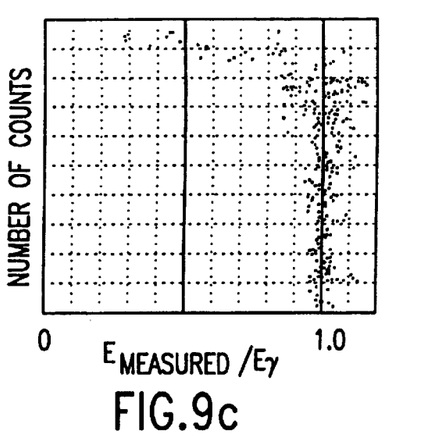
FIG. 9c shows the corrected energy of gamma interaction correlated with the depth of interaction for the monolithic detector array shown in FIG. 2a with uniform illumination of gamma rays with $E_\gamma$=140 keV with the detector operating in the mode of efficient electron collection and maximum hole trapping.
Figure 9D:
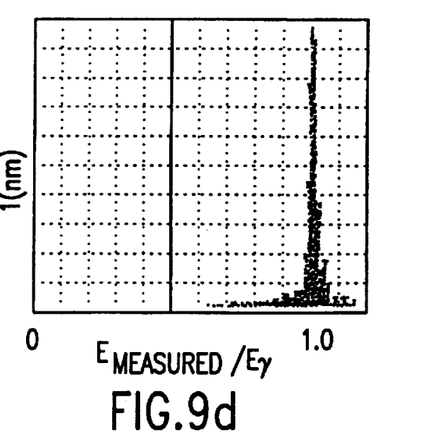
FIG. 9d shows the spectrum of corrected energy of gamma interaction for the monolithic detector array shown in FIG. 2a with uniform illumination of gamma rays with E=140 keV with the detector operating in the mode of efficient electron collection and maximum hole trapping.
Figure 9E:
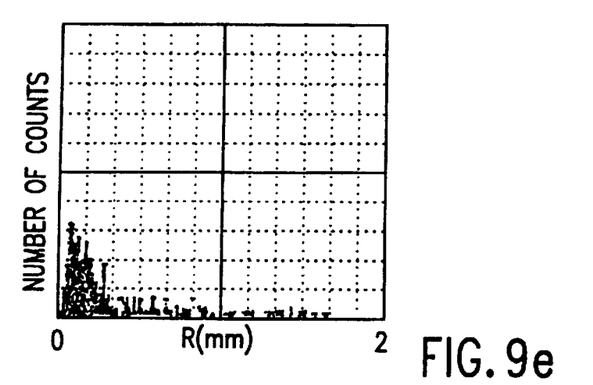
FIG. 9e shows the distance between the measured planar location and actual planar location of gamma interaction for the monolithic detector array shown in FIG. 2a with uniform illumination of gamma rays with E=140 keV with the detector operating in the mode of efficient electron collection and maximum hole trapping.

FIGS. 9a to 9e show the results of simulation of the monolithic detector array depicted in FIG. 2a. The detector consists of CdZnTe of 3 mm thickness, with the positive electrode segmented to a 4×4 array of 2×2 mm² pads. Gamma ray photons with $E_\gamma$=140 keV are incident on the negative electrode, with uniform illumination over the whole area of the detector. The depth of interaction is given by an exponential function, where for gamma rays of 140 keV energy in CdZnTe, the mean interaction depth is 2.4 mm. Photon interaction events are randomly generated, and induced charge signals on all segmented elements are calculated. It is assumed that electrons are completely collected while holes are completely trapped. On top of the charge signals for each readout channel, random noise is added with 150 e⁻ r.m.s. For each event, the generated induced charge signals for all readout elements are compared to the calculated detector template using a least $\chi^2$ fitting techniques to obtain the best fit for energy, spatial location, and depth of the photon interaction. FIG. 9a shows the measured energy obtained from the total induced charge for these calculated events. FIG. 9b shows a correlation between the measured energy obtained from the total induced charge and depth of interaction, t. Notice that the measured energy diminishes as the depth of interaction increases, as to be expected for a detector with complete electron collection and complete hole trapping. FIG. 9c shows the correlation between the corrected energy and the depth of interaction, while FIG. 9d shows the spectrum for the corrected energy. Notice that the corrected energy shows a very sharp peak with very little signs of incomplete charge collection. FIG. 9e shows the distance, R, between the position of photon interaction and the measured position using the present invention for obtaining sub-pixel resolution. Notice that the difference between the actual and measured photon interaction point is, on the average, about 0.4 mm even though the size of the readout pad elements for this detector, are 2×2 mm².

We claim:

1. A method for obtaining the planar location with sub-pixel resolution and corrected energy of a gamma or X-ray photon interacting with a room temperature solid state detector of given thickness, having a positive electrode with segmented readout elements, wherein for each photon interaction trigger a positive-induced charge signal is induced on a central readout element and negative-induced charge signals, are induced on adjacent readout elements, said method comprising the steps of:

for each photon interaction trigger, simultaneously measuring the positive-induced charge signal on the central readout element and the negative-induced charge signals on the adjacent readout elements; and statistically correlating the positive-induced charge signals on the central readout elements and the negative-induced charge signals on the adjacent readout elements with detector response templates to obtain a best fit template, thereby obtaining the photon's energy, location and depth of interaction.

2. The method according to claim 1, wherein said templates are constructed by measurement in accordance with the following steps:

irradiate the room temperature solid state detector with a photon of known energy and planar location;

collect a sample of photon interaction events, where for each photon event measure simultaneously the maximum positive-induced charge signal induced on the central readout element and the negative-induced charge signals induced on the adjacent readout elements;

store the known energy and planar location of the incident photon and the sample of photon interaction events containing the positive-induced charge and the negative-induced charge signals in memory means;

compute for each of the sample of photon interaction events the measured energy of the incident photon by summing the positive and negative-induced charge signals on the readout elements;

derive for each of the sample of photon interaction events the depth of interaction from the thickness of the detector, the measured and the known energy of the incident photon; and after completing these steps for creating a template at this specific x-y location, scan the detector at various x-y locations and repeat the above steps at each x-y location to obtain a detector map of templates of detector response.

3. The method according to claim 1, wherein the statistical correlation is a $\chi^2$ correlation.

4. The method according to claim 1, wherein said simultaneous measurement is performed by triggering the detector when a trigger signal is obtained from the common (non-segmented) electrode.

5. The method according to claim 4, wherein the said trigger signal is initiated at 15% of the energy of the signal detected on the common electrode.

6. The method according to claim 1, wherein said simultaneous measurement is performed by triggering the detector when a trigger signal is obtained from any one of the segmented readout elements by means of a discriminator placed in each readout channel.

7. The method according to claim 6, wherein said trigger signal is initiated at a predetermined level of the energy of the signal detected by said any one of the segmented readout elements.

8. The method according to claim 6, wherein said trigger signal is initiated at 15% of the energy of the signal detected by said any one of the segmented readout elements.

9. A method for obtaining the planar location with sub-pixel resolution and corrected energy of a photon interacting with a room temperature solid state detector of given thickness having a positive electrode and a negative electrode with segmented readout elements, wherein negative-induced charge signals are induced on said readout elements, said method comprising the steps of:

simultaneously measuring the negative-induced charge signals on said readout elements;

statistically correlating the negative-induced charge signals on the readout elements with detector response templates to obtain a best fit template, thereby obtaining the photon's location and depth of interaction;

obtaining the total negative-induced charge on the readout elements; and hence, a measured energy of the incident photon; and deriving a correlated energy of the incident photon from the measured energy, depth of interaction and thickness of the detector.

10. The method according to claim 9, wherein said templates are constructed by measurement in accordance with the following steps:

irradiate the room temperature solid state detector with a photon of known energy and planar location;

collect a sample of photon interaction events, where for each photon event measure simultaneously the negative-induced charge signals induced on the adjacent readout elements;

store the known energy and planar location of the incident photon and the sample of photon interaction events containing the positive-induced charge signals in memory means;

derive for each of the sample of events the depth of interaction from the negative-induced charge signals, where the depth of interaction is equal to $D(1-E_{measured}/E_{photon})$ and D=thickness of detector, i.e. distance between the positive and negative electrodes, and store the result in the memory means; and after completing these steps for creating a template at this specific x-y location, scan the detector at various x-y locations and repeat the above steps at each x-y location to obtain a detector map of templates of detector response.

11. A method for obtaining the planar location wit sub-pixel resolution and corrected energy of a photon interacting with a room temperature solid state detector of given thickness having a positive electrode with segmented readout elements wherein a maximum positive-induced charge signal is induced on a central readout element and negative-induced charge signals are induced on adjacent readout elements, said positive and negative-induced charge signals being measured relative to a zero charge level, said method comprising the steps of:

simultaneously measuring the positive and negative-induced charge signals on said readout elements;

interpolating the negative-induced charge signals induced on adjacent readout elements to obtain a surface of revolution of the interpolated negative-induced charge signals, said surface of revolution having a centroid and an apex;

determining the planar location of said centroid thereby obtaining the planar location of the photon interaction;

extrapolating the negative induced charge contribution to the signal from the central readout element from interpolating the surface of revolution formed by adjacent readout elements to interpolated value on central readout element; and obtaining a corrected energy value by adding the magnitude of the extrapolated negative contribution to the signal obtained from the measured positive signal on the central readout element.

12. A method for obtaining the planar location with sub-pixel resolution and corrected energy of a photon interacting with a room temperature solid state detector of given thickness having a common positive electrode and a negative electrode with segmented readout elements wherein negative-induced charge signals are induced on the readout elements, said method comprising the steps of:

simultaneously measuring the negative-induced charge signals on said readout elements;

interpolating the negative-induced charge signals induced on the central and adjacent readout elements to obtain a surface of revolution of the interpolated negative-induced charge signals, said surface of revolution having a centroid;

determining the planar location of said centroid thereby obtaining the planar location of the photon interaction;

computing the measured energy of the incident photon by summing the negative-induced charge signals on all the readout elements determining the width of the body of revolution at its centroid, thereby obtaining the depth of the interaction; and obtaining a corrected energy value from the measured energy, the depth of interaction and thickness of the detector.

13. An imaging apparatus for locating a photon interacting with a room temperature solid state detector of a given thickness, the detector comprising two electrodes of negative and positive polarities, one being a common electrode and the other being a segmented electrode formed with a plurality of segmented readout elements each defining a pixel size, the interaction causing induced charge signals induced on at least some of said readout elements, the apparatus comprising:

an electronic system formed of a plurality of charge sensitive elements each coupled to an associated readout element, thereby the electronic system being adapted for simultaneously measuring said induced charge signals and for transmitting data representative thereof; and a processor coupled to the electronic system so as to be responsive to said data for statistically correlating the induced charge signals with detector response templates so as to obtain a best fit template and for determining the planar location with a sub-pixel resolution, the energy and the depth of interaction of said photon.

14. The apparatus according to claim 13, wherein said segmented electrode is the positive one of the two electrodes, the induced signals are positive-charge induced signals induced on a central readout element and negative induced charge signals induced on adjacent readout elements.

15. The apparatus according to claim 13, wherein said segmented electrode is the negative one of the two electrodes, the induced signals are negative-induces charge signals induced on said readout elements.

16. The apparatus according to claim 13, wherein said electronic system also comprises a digitizing scheme.

17. The apparatus according to claim 13, wherein said electronic system is adapted for measuring the induced signals of both polarities.

18. An imaging apparatus for locating a photon interacting with a room temperature solid state detector of a given thickness, the detector comprising two electrodes of negative and positive polarities, one being a common electrode and the other being a segmented electrode formed with a plurality of segmented readout elements each defining a pixel size, the interaction causing induced charge signals induced on at least some of said readout elements, the apparatus comprising:

an electronic system formed of a plurality of charge sensitive elements each coupled to an associated readout element, thereby the electronic system being adapted for simultaneously measuring said induced charge signals and for transmitting data representative thereof; and a processor coupled to the electronic system so as to be responsive to said data for determining a statistical centroid of a circle of revolution obtained from the induced charge signals induced on adjacent readout elements so as to extract the location of the photon interaction and for providing a correction from a linear sum of said induced charge signals induced on the adjacent readout elements so as to correct for energy measurements.

19. The apparatus according to claim 18, wherein said segmented electrode is the positive one of the two electrodes, the induced signals are positive-charge induced signals induced on a central readout element and negative induced charge signals induced on said adjacent readout elements.

20. The apparatus according to claim 18, wherein said segmented electrode is the negative one of the two electrodes, the induced signals are negative-induces charge signals induced on said readout elements.

21. The apparatus according to claim 18, wherein said electronic system also comprises a digitizing scheme.

22. The apparatus according to claim 18, wherein said electronic system is adapted for measuring the induced signals of both polarities.

* * * * *